1

(12) United States Patent
Park

(10) Patent No.: US 9,289,190 B2
(45) Date of Patent: Mar. 22, 2016

(54) ULTRASOUND STRAIN IMAGING VIA PIXEL FRAME AND WINDOW CORRELATION

(75) Inventor: Sang Shik Park, Seoul (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 153 days.

(21) Appl. No.: 13/213,915

(22) Filed: Aug. 19, 2011

(65) Prior Publication Data

US 2012/0046550 A1 Feb. 23, 2012

(30) Foreign Application Priority Data

Aug. 23, 2010 (KR) .................. 10-2010-0081432

(51) Int. Cl.
| | | |
|---|---|---|
| A61B 8/00 | (2006.01) | |
| A61B 8/08 | (2006.01) | |
| A61B 5/00 | (2006.01) | |
| G01S 7/52 | (2006.01) | |
| G06T 7/20 | (2006.01) | |

(52) U.S. Cl.
CPC .............. *A61B 8/485* (2013.01); *A61B 5/0053* (2013.01); *G01S 7/52042* (2013.01); *G06T 7/2013* (2013.01); *G06T 2207/10132* (2013.01); *G06T 2207/20021* (2013.01)

(58) Field of Classification Search
CPC .................... A61B 8/485; G06T 2207/10132; G06T 2207/20021
USPC ........................................................ 382/130
See application file for complete search history.

(56) References Cited

U.S. PATENT DOCUMENTS

| 8,133,179 B2 | 3/2012 | Jeong et al. |
| 8,582,839 B2 | 11/2013 | Hyun et al. |

(Continued)

FOREIGN PATENT DOCUMENTS

| EP | 1 629 777 | 3/2006 |
| EP | 1 815 796 | 8/2007 |
| JP | 2010-012311 | 1/2010 |

(Continued)

OTHER PUBLICATIONS

European Office Action issued in European Patent Application No. 11177150.7 dated Jan. 31, 2012.
Zhu, Y, et al. "A Modified Block Matching Method for Real-Time Freehand Strain Imaging", Dynamedia Inc. 2002.

(Continued)

*Primary Examiner* — Amanda Lauritzen Moher
*Assistant Examiner* — Serkan Akar
(74) *Attorney, Agent, or Firm* — McDermott Will & Emery LLP

(57) ABSTRACT

Embodiments for providing a strain image in an ultrasound system are disclosed. In one embodiment, a processing unit sets windows on a pre-compression frame and a post-compression frame, and performs a correlation operation between the first and second frames within the windows to compute displacements for a third frame, wherein the processing unit selects at least one of previously set windows at an $(N-i)^{th}$ row by referring to current windows positioned at a $N^{th}$ row in an axial direction, computes an initial displacement based on displacements corresponding to the selected at least one of windows, and determines a range for moving the current window on the second frame in the axial direction based on the computed initial displacement.

9 Claims, 4 Drawing Sheets

(56) References Cited

U.S. PATENT DOCUMENTS

2007/0083113 A1*   4/2007   Varghese et al. .............. 600/437
2008/0144902 A1*   6/2008   Radulescu .................... 382/130

FOREIGN PATENT DOCUMENTS

| | | |
|---|---|---|
| JP | 2010-099378 A | 5/2010 |
| JP | 2010-119630 A | 6/2010 |
| KR | 10-2008-0024327 A | 3/2008 |
| KR | 10-2008-0086683 A | 9/2008 |
| WO | WO 2007/111765 | 10/2007 |

OTHER PUBLICATIONS

Lopata, R, et al. "Performance of Two Dimensional Displacement and Strain Estimation Techniques using a Phased Array Transducer", Ultrasound in Med. & Biol., vol. 35, No. 12, pp. 2031-2041. 2009.

Chen, H, et al. "Improvement of Elastographic Displacement Estimation Using a Two-Step Cross-Correlation Method", Ultrasound in Med. & Biol,, vol. 33 No. 1, pp. 48-56. 2007.

Korean Office Action issued in Korean Patent Application No. 10-2010-0081432 dated Nov. 28, 2013, with English translation, 6 pgs.

Notice of Allowance Korean Patent Application No. 10-2010-0081432 dated Feb. 25, 2014 with English translation.

* cited by examiner

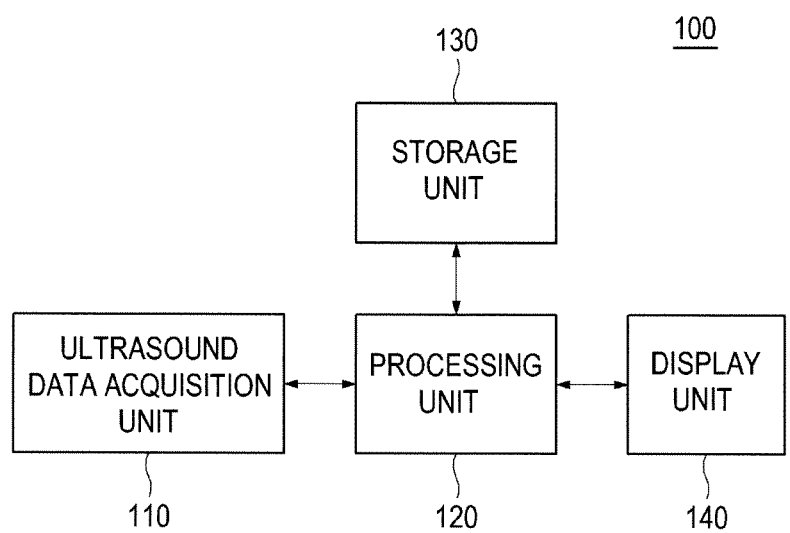
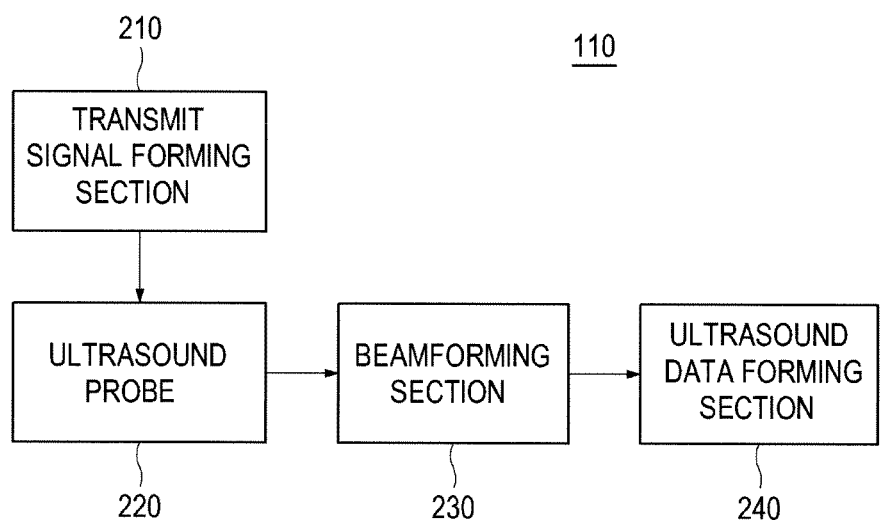

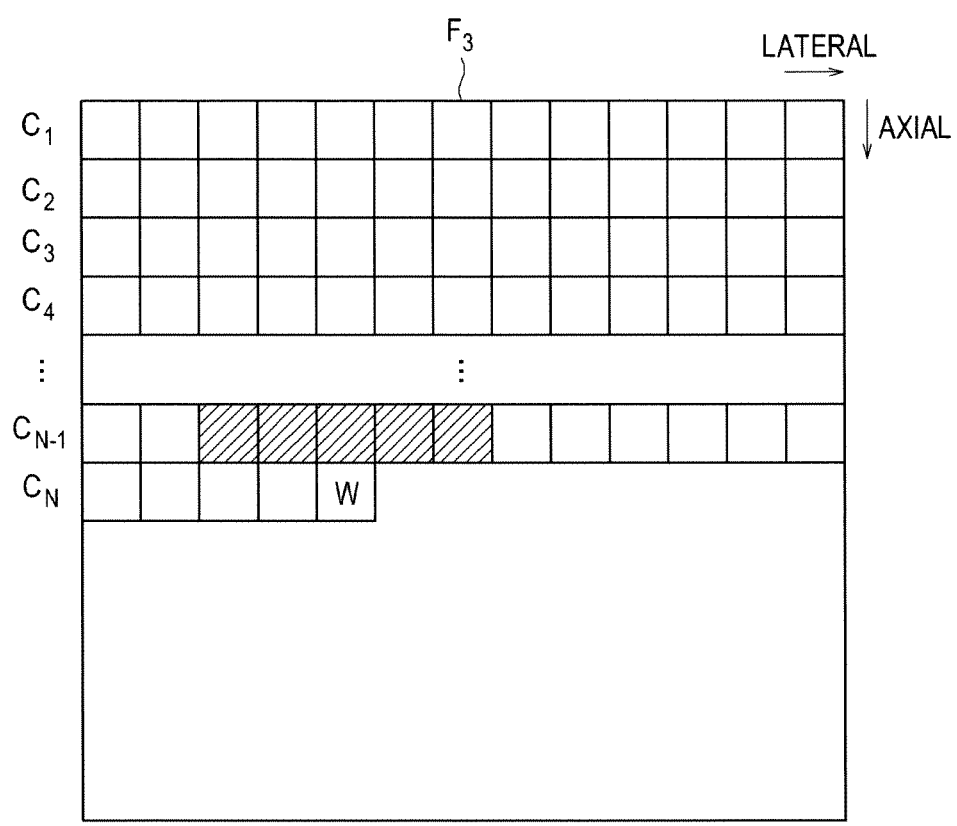

ULTRASOUND STRAIN IMAGING VIA PIXEL FRAME AND WINDOW CORRELATION

CROSS-REFERENCE TO RELATED APPLICATION

The present application claims priority from Korean Patent Application No. 10-2010-0081432 filed on Aug. 23, 2010, the entire subject matter of which is incorporated herein by reference.

TECHNICAL FIELD

The present disclosure generally relates to ultrasound systems, and more particularly to an ultrasound system configured to provide a strain image.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional images of internal features of an object (e.g., human organs).

Generally, the ultrasound image is displayed in a Brightness-mode (B-mode) by using reflectivity caused by an acoustic impedance difference between the tissues of the target object. However, if the reflectivity of the target object is hardly different from those of the neighboring tissues such as tumor, cancer or the like, then it is not easy to recognize the target object in the B-mode image.

To cope with the problem of recognizing the tumor, cancer and the like in the B-mode, an ultrasound elasticity imaging has been developed to visualize the mechanical characteristics of the tissues based on differences responsive to pre-compression and post-compression. Such imaging proved very helpful for diagnosing lesions such as tumor and cancer, which otherwise are hardly recognized in the B-mode image. The ultrasound elasticity imaging may utilize the scientific property that the elasticity of the tissues is related to a pathological phenomenon. For example, the tumor or cancer is relatively stiffer than the surrounding normal tissues. Thus, when stress is uniformly applied, a strain of the tumor or cancer may be typically smaller than those of the surrounding tissues. Strain is deformation of a target object due to stress applied per area and Young's modulus may be defined as a ratio of stress over strain. The strain is a differential value of a displacement. The displacement may indicate how much tissues in the target object are moved between pre-compression and post-compression.

The ultrasound system may set a window on each of the pre-compression frame data and post-compression frame data, and move the window in an axial direction for a correlation operation therebetween, thereby obtaining displacements. In such a case, when a position gap between the windows set on the pre-compression frame data and the post-compression frame data is beyond a range of a phase, a decorrelation error may occur.

Conventionally, the ultrasound system is configured to determine an initial displacement from a current position of the window (i.e., displacement that has already been computed in an axial direction at a current position of the window) and move the window by the initial displacement to compute a displacement in order to remove the decorrelation error. In such a case, however, if an error in the initial displacement occurs, then an error is maintained in an axial direction. Thus, a dropout, i.e., a horizontal line in a strain image, may be generated.

SUMMARY

Embodiments for forming correcting a dropout in strain imaging in an ultrasound system are disclosed herein. In one embodiment, by way of non-limiting example, an ultrasound system comprises: an ultrasound data acquisition unit configured to acquire first ultrasound data for a first frame wherein compression is not applied to a target object and second ultrasound data for a second frame wherein compression is applied to the target object; and a processing unit configured to set windows on the respective first and second frames, move the windows in axial and lateral directions and perform a correlation operation between the first and second frames within the windows to compute displacements to determine pixel values of a third frame, the processing unit being further configured to form a strain image based on the computed displacements, wherein the processing unit is configured to select at least one of previously set windows at an $(N-i)^{th}$ row by referring to current windows positioned at a $N^{th}$ row in an axial direction on the respective first and second frames, compute an initial displacement based on displacements corresponding to the selected at least one of windows, and determine a range for moving the current window on the second frame in the axial direction based on the computed initial displacement, wherein N is an integer greater than 1 and i is an integer greater than 0 but less than N.

In another embodiment, a method of providing a strain image, comprises: a) acquiring first ultrasound data for a first frame wherein compression is not applied to a target object; b) acquiring second ultrasound data for a second frame wherein compression is applied to the target object; c) setting windows on the respective first and second frames; d) moving the windows in axial and lateral directions and performing a correlation operation between the first and second frames within the windows to compute displacements to determine pixel values of a third frame, wherein the step d) includes selecting at least one of previously set windows at an $(N-i)^{th}$ row by referring to current windows positioned at a $N^{th}$ row in an axial direction on the respective first and second frames, computing an initial displacement based on displacements corresponding to the selected at least one of windows, and determining a range for moving the current window on the second frame in the axial direction based on the computed initial displacement, wherein N is an integer greater than 1 and i is an integer greater than 0 but less than N; and e) forming a strain image based on the computed displacements.

In yet another embodiment, there is provided a computer-readable storage medium storing instructions that, when executed by a computer, cause the computer to perform a method of providing a strain image, the method comprising: a) acquiring first ultrasound data for a first frame where compression is not applied to a target object; b) acquiring second ultrasound data for a second frame where compression is applied to the target object; c) setting windows on the respective first and second frames; d) moving the windows in axial and lateral directions and performing a correlation operation between the first and second frames within the windows to compute displacements to determine pixel values of a third frame, wherein the step d) includes selecting at least one of previously set windows at an $(N-i)^{th}$ row by referring to current windows positioned at a $N^{th}$ row in an axial direction on the respective first and second frames, computing an initial displacement based on displacements corresponding to the selected at least one of windows, and determining a range for moving the current window on the second frame in the axial direction based on the computed initial displacement, wherein N is an integer greater than 1 and i is an integer greater than 0 but less than N; and e) forming a strain image based on the computed displacements.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIG. 1 is a block diagram showing an illustrative embodiment of an ultrasound system.

FIG. 2 is a block diagram showing an illustrative embodiment of an ultrasound data acquisition unit of FIG. 1.

FIGS. 3 to 5 are diagrams showing examples of determining an initial displacement.

DETAILED DESCRIPTION

Figure 4:
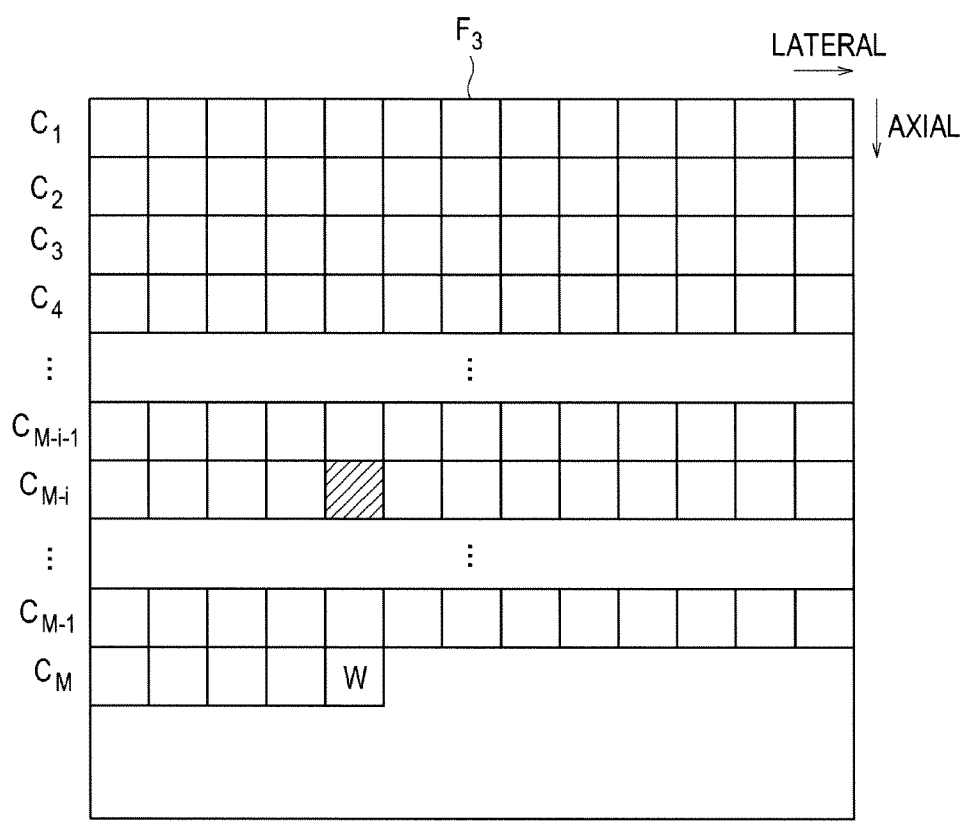

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Referring to FIG. 1, an ultrasound system constructed in accordance with one embodiment is shown. The ultrasound system 100 may include an ultrasound data acquisition unit 110, a processing unit 120, a storage unit 130 and a display unit 140.

The ultrasound data acquisition unit 110 may be configured to transmit ultrasound beams to a target object and receive ultrasound echoes reflected from the target object to thereby form ultrasound data representative of the target object. An operation of the ultrasound acquisition unit will be described in detail by referring to FIG. 2.

FIG. 2 is a block diagram showing an illustrative embodiment of the ultrasound data acquisition unit 110. Referring to FIG. 2, the ultrasound data acquisition unit 110 may include a transmit signal forming section 210. The transmit signal forming section 210 may generate a plurality of transmit signals and apply delays to the transmit signals.

The ultrasound data acquisition unit 110 may further include an ultrasound probe 220, which is coupled to the transmit signal forming section 210. The ultrasound probe 220 may include an array transducer containing a plurality of transducer elements for reciprocal conversion between electric signals and ultrasound signals. The ultrasound probe 220 may be configured to transmit ultrasound signals in response to the transmit signals. The ultrasound probe 220 may be further configured to receive ultrasound echoes reflected from the target object to thereby output receive signals. In one embodiment, the receive signals may include first receive signals obtained without applying compression to the target object and second receive signals obtained with applying compression to the target object. The compression may be applied by using the ultrasound probe 220. In such a case, a compression plate may be mounted around a front side of the ultrasound probe 220. In another embodiment, an additional device for compressing the target object may be employed.

The ultrasound data acquisition unit 110 may further include a beam forming section 230, which is coupled to the ultrasound probe 220. The beam forming section 230 may be configured to digitize the electrical receive signals into digital signals. The beam forming section 230 may also apply delays to the digital signals in consideration of distances between the elements of the ultrasound probe 220 and focal points. The beam forming section 230 may further sum the delayed digital signals to form receive-focused signals. In one embodiment, the beam forming section 230 may form first receive-focused signals based on the first receive signals and second receive-focused signals based on the second receive signals.

The ultrasound data acquisition unit 110 may further include an ultrasound data forming section 240, which is coupled to the beam forming section 230. The ultrasound data forming section 240 may be configured to form ultrasound frame data sets corresponding to a plurality of frames based on the receive-focused signals. The ultrasound frame data sets may include RF data sets or in-phase/quadrature (IQ) data sets. However, the ultrasound data may not be limited thereto. The ultrasound data forming section 240 may be further configured to perform a variety of signal processing (e.g., gain adjustment, filtering, etc.) upon the receive-focused signals. In one embodiment, the ultrasound data may include a first ultrasound frame data set formed based on the first receive-focused signals and a second ultrasound frame data set formed based on the second receive-focused signals.

Referring back to FIG. 1, the processing unit 120, which is coupled to the ultrasound data acquisition unit 110, is configured to set windows having predetermined sizes on a first frame corresponding to the first ultrasound data and a second frame corresponding to the second ultrasound data, respectively. The processing unit 120 is further configured to move the windows set on the respective first and second frames in lateral and axial directions of the frames and perform a correlation operation between the windows to compute displacements in the corresponding windows for forming a frame corresponding to a strain image (hereinafter, referred to as "third frame"). In one embodiment, when the window is currently positioned at a location corresponding to an $N^{th}$ row in an axial direction in the third frame F3, the processing unit 120 may be configured to select predetermined numbers of windows, which were set at a $(N-i)^{th}$ row, by referring to the currently positioned window, wherein N is an integer greater than 1 and i is an integer equal to or greater than 1. The processing unit 120 is configured to determine an initial displacement for moving the window on the second frame based on the displacements within the predetermined numbers of windows. The initial displacement may be a displacement for moving the window on the second frame without causing a decorrelation error.

In one embodiment, the processing unit 120 is configured to select predetermined numbers (e.g., five) of windows (hatched regions), which were previously set to determine pixel values at a $(N-1)^{th}$ row $C_{N-1}$ of the third frame F3 on the respective first and second frames, by referring to a current window, which is set to determine pixel values at an $N^{th}$ row $C_N$ in an axial direction, as shown in FIG. 3. The processing unit 120 is configured to determine an initial displacement based on displacements associated with the selected five windows. In such a case, the initial displacement for a first row $C_1$ may be determined according to the conventional method. In one embodiment, the initial displacement may be a median value of displacements at the selected windows; however, it may not be limited thereto.

In another embodiment, the processing unit 120 may be configured to select one window (hatched region), which was set to determine pixel values at a $(M-k)^{th}$ row $C_{M-k}$ of the third frame F3 on the respective first and second frames, by referring to a current window, which is set to determine pixel values at an $N^{th}$ row of the third frame in an axial direction, as shown in FIG. 4, wherein k is an integer greater than 1. The processing unit 120 is further configured to determine a displacement corresponding to the selected window as an initial displacement.

Figure 5:
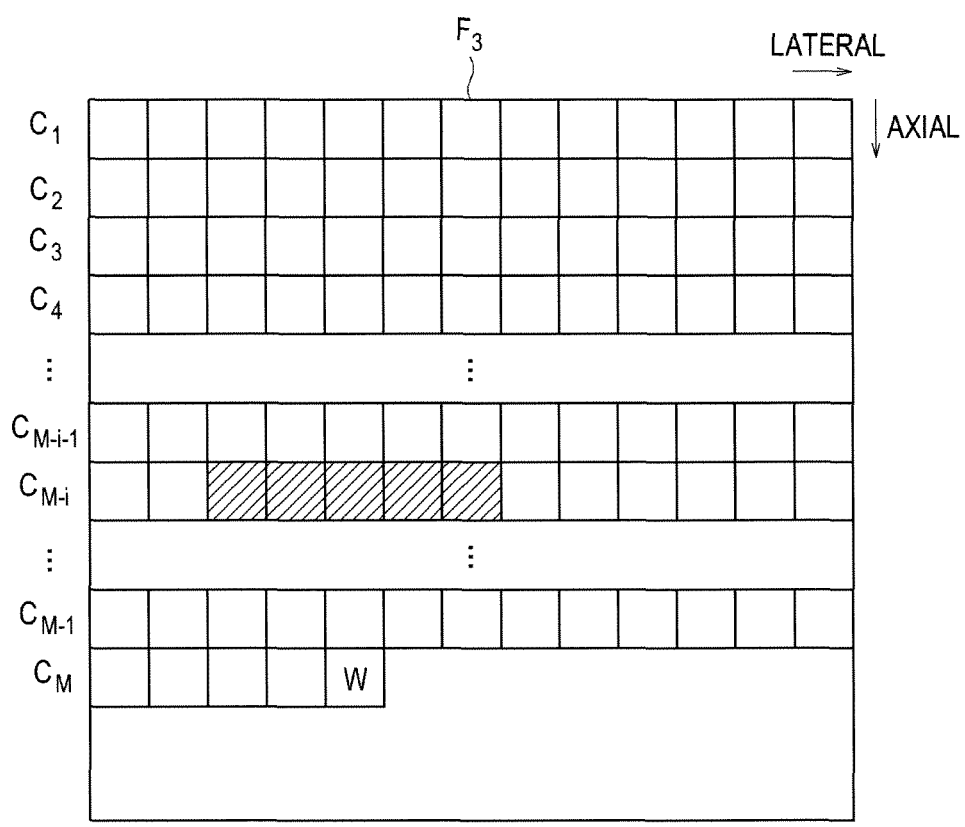

In another embodiment, the processing unit 120 may be configured to select predetermined numbers of windows (hatched regions), which were set at a $(M-k)^{th}$ row $C_{M-k}$ in the third frame F3, by referring to a current window, which is set at an $N^{th}$ row in an axial direction, as shown in FIG. 5, wherein k is an integer greater than 1. The processing unit 120 is further configured to determine an initial displacement based on displacements at the selected windows. The initial displacement may a median value of displacements at the selected windows.

Referring back to FIG. 1, the processing unit 120 is configured to determine a moving range of the window on the second frame in an axial direction based on the determined initial displacement and move the window on the second frame based on the moving range. The processing unit 120 is configured to compute a displacement at the moved window and form a strain image based on the displacement. Since the formation of the strain image based on the displacement may be performed by using various well-known methods, its detailed explanation will be omitted herein.

The storage unit 130 is configured to store the ultrasound data acquired in the ultrasound data acquisition unit 110. The storage unit 130 is configured to further store the displacements, which are computed in the processing unit 120. The display unit 140 is configured to display the strain image, which is formed in the processing unit 120. Also, the display unit 140 displays the frames formed in the processing unit 120.

In another embodiment, there is provided a computer-readable storage medium storing instructions that, when executed by a computer, cause the computer to perform a method of providing a strain image, the method comprising: a) acquiring first ultrasound data for a first frame where compression is not applied to a target object; b) acquiring second ultrasound data for a second frame where compression is applied to the target object; c) setting windows on the respective first and second frames; d) moving the windows in axial and lateral directions and performing a correlation operation between the first and second frames within the windows to compute displacements to determine pixel values of a third frame, wherein the step d) includes selecting at least one of previously set windows at an $(N-i)^{th}$ row by referring to current windows positioned at a $N^{th}$ row in an axial direction on the respective first and second frames, computing an initial displacement based on displacements corresponding to the selected at least one of windows, and determining a range for moving the current window on the second frame in the axial direction based on the computed initial displacement, wherein N is an integer greater than 1 and i is an integer greater than 0 but less than N; and e) forming a strain image based on the computed displacements.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising;
   an ultrasound data acquisition unit, including a transmit signal former, an ultrasound probe, a beam former and an ultrasound data former, configured to acquire first ultrasound data for a first frame wherein compression is not applied to a target object and second ultrasound data for a second frame wherein compression is applied to the target object; and
   a computer configured to set windows on the respective first and second frames, move the windows in axial and lateral directions and perform a correlation operation between the first and second frames within the windows to compute displacements of windows on a third frame to determine pixel values of the third frame, the computer being further configured to form a strain image based on the computed displacements, wherein the third frame corresponds to the strain images,
   wherein the computer is configured to select at least one of previously set windows at an $(N-i)$th row on the third frame by referring to current windows positioned at a Nth row in an axial direction on the third frame, compute an initial displacement based on displacements corresponding to the selected at least one of windows wherein the initial displacement includes a median value of displacements, and determine a range for moving the current window on the second frame in the axial direction based on the computed initial displacement, wherein N is an integer greater than 1 and i is an integer greater than 0 but less than N, and
   wherein the initial, displacement is a displacement for moving the window on the second frame without causing a decorrelation error.

2. The ultrasound system of claim 1, wherein the computer is configured to select previously set windows adjacent to the current window at an $(N-1)^{th}$ row on the third frame.

3. The ultrasound system of claim 1, wherein the computer is configured to select one previously set window positioned at an identical column to the current window at an $(N-k)^{th}$ row on the third frame.

4. The ultrasound system of claim 1, wherein the computer is configured to select a plurality of previously set windows positioned at an $(N-k)^{th}$ row on the third frame.

5. A method of providing a strain image in an ultrasound system including an ultrasound acquisition unit and a computer, comprising;
   a) acquiring, with the ultrasound acquisition unit, first ultrasound data for a first frame wherein compression is not applied to a target object;
   b) acquiring, with the ultrasound acquisition unit, second ultrasound data for a second frame wherein compression is applied to the target object;
   c) setting, with the computer, windows on the respective first and second frames;
   d) moving, with the computer, the windows in axial and lateral directions and performing a correlation operation between the first and second frames within the windows to compute displacements of windows on a third frame to determine pixel values of the third frame, wherein the step d) includes selecting at least one of previously set windows at an (N-i)th row on the third frame by referring to current windows positioned at a Nth row in an axial direction on the third frame computing an initial displacement based on displacements corresponding to the selected at least one of windows wherein the initial displacement includes a median value of displacements, and determining a range for moving the current window on the second frame in the axial direction, based on the computed initial displacement, wherein N is an integer greater than 1 and i is an integer greater than 0 but less than N; and e) forming a strain image based on the computed displacements, wherein the third frame corresponds to the strain image, wherein the initial, displacement is a displacement for moving the window on the second frame without, causing a decorrelation error.

6. The method of claim 5, wherein the step d) includes selecting previously set windows adjacent to the current window at an $(N-1)^{th}$ row on the third frame.

7. The method of claim 5, wherein the step d) includes selecting one previously set window positioned at an identical column to the current window at an $(N-k)^{th}$ row on the third frame.

8. The method of claim 5, wherein the step d) includes selecting a plurality of previously set windows positioned at an $(N-k)^{th}$ row on the third frame.

9. A non-transitory computer-readable storage medium storing instructions that, when executed by a computer, cause the computer to perform a method of providing a strain image, the method comprising:

a) acquiring, with the ultrasound acquisition unit, first ultrasound data for a first flume wherein compression is not applied to a target object;

b) acquiring, with the ultrasound acquisition unit, second ultrasound data for a second frame wherein compression is applied to the target object;

c) setting, with the computer, windows on the respective first and second frames;

d) moving, with the computer, the windows in axial and lateral directions and performing a correlation operation between the first and second frames within the windows to compute displacements of windows on a third frame to determine pixel values of the third frame, wherein the step d) includes selecting at least one of previously set windows at an (N−i)th row on the third frame by referring to current windows positioned at a Nth row in an axial direction on the third frame computing an initial displacement based on displacements corresponding to the selected at least one of windows wherein the initial displacement includes a median value of displacements, and determining a range for moving the current window on the second frame in the axial direction, based on the computed initial displacement, wherein N is an integer greater than 1 and i is an integer greater than 0 but less than N; and e) forming a strain image based on the computed displacements, wherein the third frame corresponds to the strain image, wherein the initial, displacement is a displacement for moving the window on the second frame without, causing a decorrelation error.

* * * * *